United States Patent [19]

Cotter

[11] 4,211,721

[45] Jul. 8, 1980

[54] PROCESS FOR THE PREPARATION OF AROMATIC NITRILES

[75] Inventor: Byron R. Cotter, Grand Island, N.Y.

[73] Assignee: Hooker Chemicals & Plastics Corp., Niagara Falls, N.Y.

[21] Appl. No.: 966,433

[22] Filed: Dec. 4, 1978

[51] Int. Cl.² ............................................ C07C 120/04
[52] U.S. Cl. ........................... 260/465 G; 260/465 H; 260/465 R; 252/429 R
[58] Field of Search ........................ 260/465 R, 465 G

[56] References Cited

PUBLICATIONS

Takayi, Bull. Chem. Soc. Jap., vol. 48, p. 3298 (1975).
Takayi et al., Bull. Chem. Soc. Jap., vol. 49, p. 3177 (1976).
Sekiya et al., Chem. Lett., vol. 3, pp. 277-278 (1975).
Yamamura et al., Tetrahedron Letters No. 50, pp. 4429-4430 (1970).

*Primary Examiner*—Dolph H. Torrence
*Attorney, Agent, or Firm*—Peter F. Casella; William J. Crossetta, Jr.; Arthur S. Cookfair

[57] ABSTRACT

A method and a useful catalyst composition for the production of aromatic nitriles for the corresponding nuclearly halogenated aromatic compounds which contain from 1 to 4 halogen atoms substituted selected from chlorine, bromine and iodine are described.

The method involves the steps of heating the halogenated aromatic compound to a temperature of at least 100° C. for a period of at least 2 hours in the presence of potassium cyanide and a catalyst composition comprised of:
- (a) a ether component selected from the group consisting of 18-crown-6 ether, polyethers, alkyoxypolyethers and mixtures thereof having a molecular weight between about 200 and about 25,000, and
- (b) a palladium salt complex comprised of:
  - (1) a palladium salt selected from palladium iodide, chloride, bromide and mixtures thereof, and
  - (2) an organophosphine selected from the group consisting of alkyarylphosphines and triarylphosphines containing from about 8 to about 80 carbon atoms.

6 Claims, No Drawings

PROCESS FOR THE PREPARATION OF AROMATIC NITRILES

BACKGROUND OF THE INVENTION

The present invention relates to an improved process for the production of aromatic nitriles from nuclearly halogenated aromatic hydrocarbons and to catalytic compositions for carrying out the process.

Nitriles, organic cyanides, are useful organic compounds becuase of their high reactivity. Nitriles are readily hydrolyzed with acids or alkalies to form various useful carboxylic acid amides, acids and salts. For example, terephalonitrile is an intermediate for condensation polymers based on terephthalic acid, and benzoic acid, a derivative of benzonitrile, is a widely used commercial chemical. Many of the nitrile products are, for example, benzonitrile, useful solvents.

Nitriles have been synthesized from carboxylic acid ammonium salts or amides by distillation with a strong dehydrating agent, such as phosphorus pentoxide. However, since such processes involve the use of relatively expensive raw materials, the nitrile products are not produced on a competitive basis. Nitriles may be produced by passing carboxylic acids or esters in a vapor phase with ammonia over a bed of alumina maintained at a temperature of about 500° C. This process also involves relatively expensive starting materials and has an additional detriment of low yield. The commercial production of nitriles has generally been carried out using low cost organic halides reacted, for example, with potassium cyanide under pressure, in liquid phase in dilute alcohol solutions, to convert the halide to a nitrile. The major shortcomings of such processes is that the yields are usually poor, because of competing reactions and the usual presence of malodorous isonitriles in the product. Nitriles are also produced commerically by reacting organic halides with hydrogen cyanide in vapor phase reactions at temperatures of 650° C. or above, or at lesser temperatures, e.g., about 480° C. to about 650° C., in the presence of metal or metal oxide catalysts. Although such vapor phase reactions have attained a fair conversion of halide to cyanide, the yield and selectivity have not reached more than a barely satisfactory level.

More recently, it has been proposed in the literature to produce nitriles by the replacement of halides on aryl compounds with cyanide ions using palladium salt catalysts. The reactions are carried out in a dipolar, aprotic solvent, such as hexamethylphosphoric triamide, tetramethylurea, N,N-dimethylformamide, N,N-dimethylacetamide, propylene carbonate or N-mthoylpyrrolidone. Examples of such reactions are given by K. Takagi, *Bull. Chem. Soc. Jap.*, Vol. 48, pages 3298 (1975) and K. Takagi, et al, *Bull. Chem. Soc. Jap.*, Vol. 49, page 3177 (1976).

GENERAL DESCRIPTION OF THE INVENTION

It has now been found that co-catalysts comprised of a polyether component, such as 18-crown-6 (1,4,7,10,13,16-hexaoxacylooctadecane), polyethers, such as poly (ethylene glycol), or alkyoxypolyethers, such as methoxypolyethylene glycol, such polyethers or alkyoxypolyethers having a molecular weight ranging from about 200 to about 25,000 are useful together with a palladium salt complex component, for example, palladium salt-triarylphosphine or alkyarlyphosphine complexes, to convert aryl chloride compounds to the corresponding nitrile compounds without the need for a solvent system.

The halogenated aromatic starting material is initially heated in the presence of the co-catalyst, preferably under an inert atmosphere, to a temperature of about 100° C. or above, in the presence of potassium cyanide and maintained at the reaction temperature until the desired conversion takes place.

The halogenated organic starting material is suitably selected from the mono-, di-, and tricyclic compounds, preferably carbocyclic compounds of the benzene and naphthalene series. The starting materials may have from one to four but, more preferably, one to two halogen atoms substituted on the aryl nucleus. The halogen atoms may be chlorine, bromine, or iodine, but, more preferably, are chlorine or bromine. The reactivity, ease of replacement of the halogen component, ranking from the least difficult to the more difficult, is in the order of iodine, bromine and chlorine.

The polyether portion of the co-catalyst may suitably be selected from 18-crown-6 ether, or from polyethers or alkyoxypolyethers, or mixtures thereof, having a molecular weight in the range between about 200 to about 25,000 and, more particularly, between 350 and about 7500. Usually, polyethers and alkyoxypolyethers having molecular weights less than about 200 do not exhibit satisfactory catalytic activity, and molecular weights above about 25,000 are marginally useful.

The palladium salt complex portion of the co-catalyst is a complex comprised of an inorganic palladium salt, preferably selected from palladium iodide, bromide or chloride or mixtures thereof, and an organophosphine selected from alkyarylphosphines or triarylphosphines containing from about 8 to about 80 carbon atoms and, more particularly, from about 8 to about 40 carbon atoms. Examples of useful alkyarylphosphines are cyclohexyldiphenylphosphine, bis (1, 2-diphenylphosphine) ethane, and bis (1,4-diphenylophosphine) butane. Examples of useful triarylphosphines are triphenylphosphine, tritolylphosphine, and methyldiphenylphosphine. The palladium salt complex generally contains from about 5.0 to about 50.0 percent by weight and, more preferably, from about 5.0 to about 20.0 percent by weight of palladium salt. The complex may be produced by initially mixing the palladium salt and the phosphine portions or by separately adding and stirring the components into the reaction mixture.

The present co-catalyst may be prepared by forming a mixture of the palladium slat complex and the either component. However, equally useful is the generation of the co-catalyst in situ in the reaction vessel by adding and stirring the catalyst components with the halogenated organic starting material.

The amount of ether-palladium salt co-catalyst utilized may vary widely. Usually, good yields are obtained when the co-catalyst ranges between about 1.0 and about 20.0 percent. Generally, amounts of co-catalyst less than about 1.0 percent do not provide satisfactory catalytic activity, and amounts over about 20.0 percent usually do not produce results that economically justify such large amounts of co-catalyst.

The potassium cyanide reactant is utilized in amounts ranging from about ½ to 4 times and, more particularly, between about ½ and about 1½ times the stoichiometric amount required by the halogenated starting material.

Reaction temperatures vary with the halogen to be replaced. Under atmospheric conditions, temperatures in the range of between about 100° C. to about 150° C. are usually sufficient to convert brominated starting materials, whereas temperatures in the range of from about 130° C. to about 200° C. and, more preferably, in the range between about 135° C. to about 180° C. are sufficient to convert chlorinated starting materials.

The reaction is carried out in an atmosphere inert to the reaction components. Atmospheres of nitrogen, helium or argon are useful. The reaction may be carried out under atmospheric pressures; however, superatmospheric pressures are also aptly suited to use.

Reaction times vary with temperature and, to a lesser extent, with pressure. Satisfactory yields utilizing a brominated starting material are obtained with times as short as 2 hours. Usually, reaction times ranging between about 2 and about 80 hours are employed and, more particularly, reaction times between about 2 and about 60 hours are useful.

DETAILED DESCRIPTION OF THE INVENTION

The following examples are illustrative only:

EXAMPLE 1

A mixture of 0.30 g (1.69 m mole) of palladium chloride, 3.0 g (11.4 m mole) of triphenylphosphine, 20 ml (150 m mole) of p-chlorobenzotrifluoride, and 0.2 g (0.76 m mole) of 18-crown-6 were heated, with constant stirring, to a temperature of 138° C. for a period of one hour under an argon atmosphere. 120 g (184 m mol3) of potassium cyanide were then added, and the slurry stirred for a period of 69 hours while maintaining a temperature of 138° C. Gas chromatographic analysis of the product indicated that 11.8 g (69.0 m mole) of p-cyanobenzotrifluoride had been formed and that 84. g (46.5 m mole) of unreacted p-chlorobenzotriflouride was present.

EXAMPLE 2

The procedure of Example 1 was followed, except that 20 ml (169 m mole) of p-chlorotoluene was utilized as the aryl chloride starting material, and the reaction temperature was maintained at 158° C. After a reaction period of 12.5 hours, a gas chromatographic analysis indicated the presence of 2.24 g (19.1 m mole) of p-cyanotoluene and 18.4 g (146 m mole) of unreacted p-chlorotoluene.

EXAMPLE 3

The procedure of Example 1 was repeated, except that 0.25 g of poly (ethylene glycol), a product of Polysciences, Inc., having a mole weight of 7500, was substituted in place of 18-crown-6, 100 m mole of potassium cyanide were utilized. The reaction was carried out over a period of 19 hours. Gas chromatographic analysis indicated 1.31 g (7.66 m mole) of p-cyanobenzotrifluoride and 21.4 g of unreacted p-chlorobenzotrifluoride.

Although the present invention has been described with respect to several embodiments, it is not to be construed as limited to these, as it will be evident to one of ordinary skill in the art that substitution and equivalents are possible without departing from the spirit of the invention or the scope of the appended claims.

What is claimed is:

1. A method of producing aromatic nitriles which comprises the steps of reacting a nuclearly halogenated carbocyclic compound of the benzene or naphthalene series having from 1 to 4 halogen atoms substituents selected from the group of chlorine, bromine and iodine, to a temperature of at least 100° C. with potassium cyanide in the presence of a catalyst composition comprised of:
    (a) an ether component selected from the group consisting of 18-crown-6 ether, polyethers, alkyoxypolyethers and mixtures thereof having a molecular weight between about 200 and about 25,000, and
    (b) a palladium salt complex comprised of:
        (1) a palladium salt selected from palladium iodide, chloride, bromide and mixtures thereof, and
        (2) an organophosphine selected from the group consisting of alkyarylphosphines and triarylphosphines containing from about 8 to about 80 carbon atoms.

2. The method of claim 1 wherein the halogen substituent is chlorine.

3. The method of claim 1 wherein the halogenated carbocyclic compound is p-chlorobenzotrifluoride.

4. The method of claim 1 wherein the catalyst component (a). is 18-crown-6 ether.

5. The method of claim 1 wherein the catalyst component (b). is comprised of palladium chloride and triphenylphosphine.

6. The method of claim 1 wherein the catalyst composition contains palladium chloride.

* * * * *